(12) United States Patent
Hwang

(10) Patent No.: US 8,808,328 B2
(45) Date of Patent: Aug. 19, 2014

(54) SPRING LOADED MECHANISM FOR MANAGING SCOLIOSIS

(71) Applicant: Tufts Medical Center, Inc., Boston, MA (US)

(72) Inventor: Steven W. Hwang, Jamaica Plain, MA (US)

(73) Assignee: Tufts Medical Center, Inc., Boston, MA (US)

( * ) Notice: Subject to any disclaimer, the term of this patent is extended or adjusted under 35 U.S.C. 154(b) by 0 days.

(21) Appl. No.: 13/855,010

(22) Filed: Apr. 2, 2013

(65) Prior Publication Data

US 2013/0268003 A1    Oct. 10, 2013

Related U.S. Application Data

(60) Provisional application No. 61/620,539, filed on Apr. 5, 2012.

(51) Int. Cl.
*A61B 17/70* (2006.01)

(52) U.S. Cl.
USPC ............. 606/251; 606/250; 606/105; 606/90; 606/57

(58) Field of Classification Search
USPC ............. 606/251, 250, 105, 90, 57; 403/366, 403/345, 348, 341, 335, 327, 325, 310, 303, 403/292, 277, 222, 202, 166, 136, 129, 125, 403/111, 109.5, 109.3, 85, 74, 72, 67, 63, 403/59, 43, 9
See application file for complete search history.

(56) References Cited

U.S. PATENT DOCUMENTS

| | | | |
|---|---|---|---|
| 702,472 A * | 6/1902 | Fortin | 606/29 |
| 5,672,175 A * | 9/1997 | Martin | 606/86 A |
| 6,030,402 A * | 2/2000 | Thompson et al. | 606/185 |
| 6,126,660 A * | 10/2000 | Dietz | 606/90 |
| 7,494,463 B2 * | 2/2009 | Nehls | 600/227 |
| 7,585,314 B2 * | 9/2009 | Taylor et al. | 606/250 |
| 7,717,938 B2 * | 5/2010 | Kim et al. | 606/250 |
| 7,867,255 B2 * | 1/2011 | Miller et al. | 606/250 |
| 8,357,181 B2 * | 1/2013 | Lange et al. | 606/248 |
| 8,500,810 B2 * | 8/2013 | Mastrorio et al. | 623/17.11 |
| 2005/0261682 A1 | 11/2005 | Ferree | |
| 2008/0177319 A1 * | 7/2008 | Schwab | 606/257 |
| 2009/0100960 A1 * | 4/2009 | Koros et al. | 74/536 |
| 2011/0137347 A1 | 6/2011 | Hunziker | |
| 2013/0274801 A1 * | 10/2013 | Buss et al. | 606/251 |

* cited by examiner

*Primary Examiner* — Jerry Cumberledge
*Assistant Examiner* — Tessa Matthews
(74) *Attorney, Agent, or Firm* — Occhiuti & Rohlicek LLP

(57) ABSTRACT

A spinal implant includes a first rod, a second rod, and connector. The first rod has a first end configured to be connected to a first bone, a second end opposed to the first end, and a longitudinal axis that passes through the first and second ends. The second rod has a first end configured to be connected to the second bone, a second end opposed to the first end. The second rod is parallel to the longitudinal axis and non-coaxial with the first rod, and at least a portion of the second end of the second rod overlaps the second end of the first rod. The connector connects the second end of the first rod to the second end of the second rod, and is configured to urge the first rod and the second rod in opposed directions that are parallel to the longitudinal axis.

11 Claims, 6 Drawing Sheets

US 8,808,328 B2

SPRING LOADED MECHANISM FOR MANAGING SCOLIOSIS

CROSS REFERENCE TO RELATED APPLICATIONS

This application claims priority to U.S. Provisional Application No. 61/620,539 filed Apr. 5, 2012, the contents of which are hereby incorporated by reference in its entirety.

BACKGROUND OF THE INVENTION

Scoliosis of the human spine results in abnormal three-dimensional deformation of the spine, but is most prominent with respect to the lateral curvature of the spine. This can be compared to a normal spine configuration in which the spinal column extends generally linearly when viewed in the frontal plane. Management of scoliosis in a child can be problematic and is complicated by growth of the child. The goal of scoliosis treatment is to prevent progression of the lateral spinal curvature and to correct or stabilize a severe lateral spinal curvature. In some cases, correction of spinal curvature is attempted by inserting a spinal implant that distracts one portion of the spine relative to another. However, to compensate for growth, many such spinal implants require repeat surgeries to permit expansion of the implant as often as every six months. In addition, such implants are often associated with complications including undesired, premature autofusion of the spine.

SUMMARY

In some aspects, a spinal implant provides distraction between a first bone and a second bone. The spinal implant includes a first rod having a first end configured to be connected to the first bone, a second end opposed to the first end, and a first rod longitudinal axis that passes through the first and second ends. The spinal implant includes a second rod having a first end configured to be connected to the second bone, a second end opposed to the first end, and a second rod longitudinal axis that is non-coaxial with the first rod longitudinal axis. At least a portion of the second end of the second rod overlaps the second end of the first rod when viewed along an axis transverse to the first rod longitudinal axis. The spinal implant also includes a coupling that connects the second end of the first rod to the second end of the second rod. The coupling is configured to urge the first rod and the second rod in opposed directions that are parallel to the first rod longitudinal axis.

The spinal implant may include one or more of the following features: The coupling includes a housing. The housing includes a first throughchannel extending through the housing, and a portion of the first rod is disposed in the first throughchannel, and a second throughchannel extending through the housing in parallel with, and spaced apart from, the first throughchannel. A portion of the second rod is disposed in the second throughchannel. The housing also includes a passage extending between and connecting the first throughchannel to the second throughchannel, and a mechanism disposed in the passage and configured to engage both the first rod and the second rod. The mechanism includes a first latch member, a second latch member, and an elastic member disposed between the first latch member and the second latch member. The elastic member is configured to urge the first latch member and the second latch member in opposed directions that are parallel to the first rod longitudinal axis. The second end of the first rod and the second end of the second rod each include teeth configured to cooperatively engage with a corresponding one of the first latch member and the second latch member. Each latch member comprises a planar side that connects to the elastic member, and an outwardly-protruding convex side opposed to the planar side. The convex side is truncated to form a flat surface that is perpendicular to the planar side. The elastic member is a coil spring including a spring first end that is connected to the first latch member, and a spring second end that is connected to the second latch member. The mechanism includes a ratchet, a spindle that rotatably supports the ratchet, and an elastic member that connects the ratchet to the spindle. The elastic member is configured to bias the ratchet to rotate about the spindle. The elastic member is a torsion spring including a spring first end that is connected to the ratchet, and a spring second end that is connected to the spindle. The second end of the first rod and the second end of the second rod each include teeth configured to cooperatively engage with a corresponding side of the ratchet.

In some aspects, a spinal implant provides distraction between a first bone and a second bone. The spinal implant includes a housing, a first throughchannel extending through the housing, and a second throughchannel extending through the housing in parallel with and spaced apart from the first throughchannel. The spinal implant includes a passage within the housing that extends between and connects the first throughchannel to the second throughchannel, and a first rod disposed in the first throughchannel. The first rod has a first end configured to be connected to the first bone, a second end opposed to the first end, and a first rod longitudinal axis that passes through the first and second ends. The spinal implant includes a second rod disposed in the second throughchannel, the second rod having a first end configured to be connected to the second bone, a second end opposed to the first end, at least a portion of the second end of the second rod overlapping the second end of the first rod when viewed along an axis transverse to the first rod longitudinal axis. In addition, the spinal implant includes a mechanism disposed in the passage. The mechanism connects the second end of the first rod to the second end of the second rod, and is configured to urge the first rod and the second rod in opposed directions that are parallel to the first rod longitudinal axis.

The spinal implant may include one or more of the following features: The mechanism includes a first latch member, a second latch member, and an elastic member disposed between the first latch member and the second latch member. The elastic member is configured to urge the first latch member and the second latch member in opposed directions that are parallel to the first rod longitudinal axis. The second end of the first rod and the second end of the second rod each include teeth configured to cooperatively engage with a corresponding one of the first latch member and the second latch member. Each latch member comprises a planar side that connects to the elastic member, and an outwardly-protruding convex side opposed to the planar side. The convex side is truncated to form a flat surface that is perpendicular to the planar side. The elastic member is a coil spring including a spring first end that is connected to the first latch member, and a spring second end that is connected to the second latch member. The mechanism includes a ratchet, a spindle that rotatably supports the ratchet, and an elastic member that connects the ratchet to the spindle, and the elastic member is configured to bias the ratchet to rotate about the spindle. The elastic member is a torsion spring including a spring first end that is connected to the ratchet, and a spring second end that is connected to the spindle. The second end of the first rod and the second end of the second rod each include teeth configured to cooperatively engage with a corresponding side of the ratchet.

Among other advantages, the spinal implant described herein includes a spring loaded mechanism that corrects spinal curvature while automatically compensating for growth. In particular, overlapping rods allow for continued growth while a spring-loaded mechanism maintains a relatively constant distraction force along the spine, preventing loss of distraction while permitting growth and relatively free spinal movement. Since the spinal implant compensates for growth and permits subtle movements in the cranial-caudal direction, autofusion is reduced.

Further advantageously, once the spinal implant has been implanted, no additional or "repeat" surgeries are necessary to adjust the mechanism. This is in contrast to some conventional spinal implants that require repeat surgeries to expand the implant to allow for growth. Since only a single surgery is required for implementation, there is reduced risk for complications associated with repeat surgeries, including infection, wound healing issues and loss of bone fixation.

Still further advantageously, the spinal implant includes a first rod having a first end configured to be connected to a first bone and a second rod having a first end configured to be connected to a second bone. The first and second rods are connected using a coupling that maintains the rods in a non-coaxial configuration and urges the first rod and the second rod in opposed directions that are parallel to the first rod longitudinal axis. In some embodiments, the non-coaxial configuration of the rods permits the spinal implant to have increased lateral span relative to some telescoping (coaxial) spinal implants. The increased lateral span can be very helpful in accommodating the spinal geometries including lateral relative vertebral offsets associated with scoliosis.

Modes for carrying out the present invention are explained below by reference to an embodiment of the present invention shown in the attached drawings. The above-mentioned object, other objects, characteristics and advantages of the present invention will become apparent from the detailed description of the embodiment of the invention presented below in conjunction with the attached drawings.

DETAILED DESCRIPTION

Figure 1:
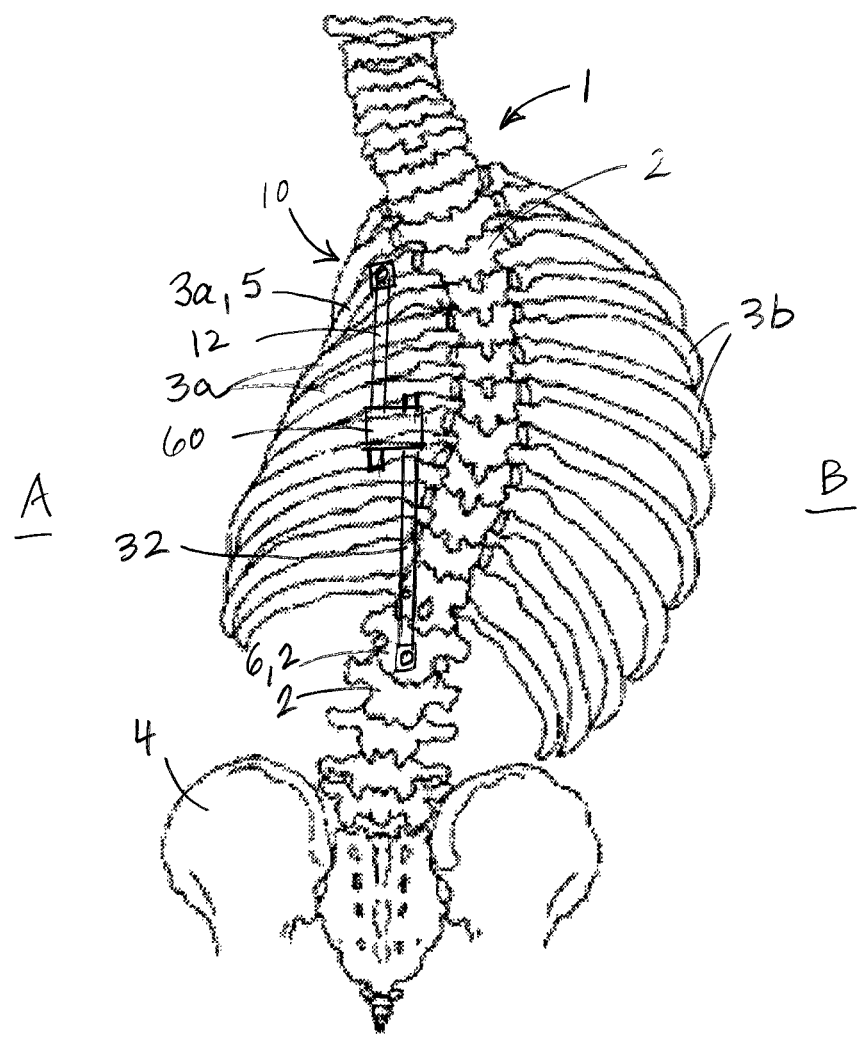
FIG. 1 is a rear view of a scoliotic human spine including a spinal implant extending between a rib and a vertebra below the ribcage.
Figure 2:
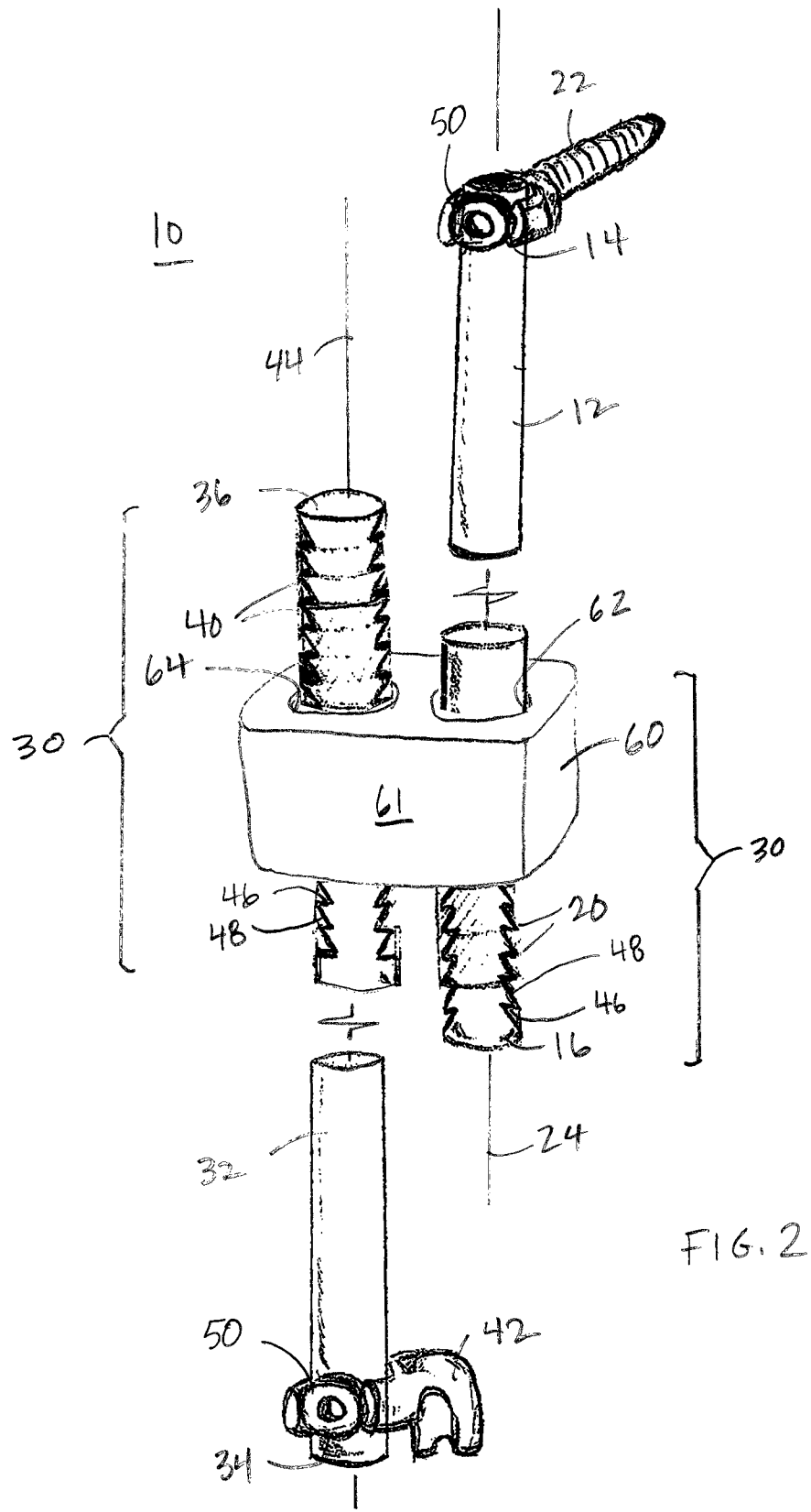
FIG. 2 is a perspective view of the spinal implant of FIG. 1.

Referring now to FIGS. 1 and 2, due to the lateral curvature of the scoliotic spine 1, the vertical spacing of the ribs 3a on a concavely-curved side A of the spine 1 become more closely spaced, while ribs 3b on the opposed, convexly-curved side B become more greatly spaced. To correct or stabilize the lateral curvature, a spinal implant 10 is surgically implanted on the vertebrae 2 of the spine 1, or on boney structures that contact the spine, for example, the ribs 3 or pelvis 4. The spinal implant 10 includes a coupling 60 that supports a first rod 12 and a second rod 32 in a parallel configuration such that the rods 12, 32 are non-coaxial but overlap when viewed in a direction transverse to the longitudinal axes 24, 44 of the rods 12, 32. Each of the first rod 12 and the second rod 32 is fixed to one of the vertebrae 2, ribs 3, or the pelvis 4 on the concavely-curved side A of the spine 1. The spinal implant 10 includes a spring-loaded mechanism 100 (best seen in FIGS. 3 and 4) disposed in the coupling 60 that urges the rods 12, 32 in opposed directions that are parallel to the longitudinal axis 24. As a result, a distraction force is applied to the spine 1 that corrects spinal curvature while automatically compensating for growth, as discussed further below.

The first rod 12 includes a first end 14, a second end 16 opposed to the first end 14, and a longitudinal axis 24 that extends between the first end 14 and the second end 16. Similarly, the second rod 32 includes a first end 34, a second end 36 opposed to the first end 34, and a longitudinal axis 44 that extends between the first end 34 and the second end 36. In the illustrated embodiment, the first and second rods 12, 32 are identical, and thus only the first rod 12 will be described in detail.

The first rod 12 is an elongated, solid cylinder having a uniform outer diameter and smooth outer surface in the regions extending from the first end 14 and including a mid portion. Adjacent to and including the second end 16, the outer surface of the first rod 12 is formed having teeth 40. Each tooth 40 extends about the circumference of the first rod 12 and is circular in a cross-section transverse to the longitudinal axis 24. Each tooth 40 includes a transverse surface 46 that extends in a plane transverse to the longitudinal axis 24, and an inclined surface 48 that is formed at an acute angle relative to the longitudinal axis 24. The transverse surface 46 and the inclined surface 48 intersect at the outer periphery of the transverse surface, which has the same outer diameter as the first end 14. In addition, the inclined surface 48 forms a conical inward taper that is widest at the transverse surface 46, and decreases in outer diameter moving toward the rod first end 14.

In some embodiments, the toothed portion 30 extends over about fifty percent of the overall length of the first rod 12. In other embodiments, the toothed portion 30 extends over about twenty-five percent of the overall length of the first rod 12. In still other embodiments, the toothed portion 30 extends over about 10 percent of the overall length of the rod 12. For example, in the illustrated embodiment, the first rod 12 has an overall length from first end 14 to second end 16 of twenty-four inches, and the toothed portion 30 extends over three inches (e.g., over twelve and a half percent of the overall length). It is understood that the overall rod length is determined at least in part by the size of the spine to be treated. In some embodiments, the first rod 12 is provided in an oversized length, and is cut to an appropriate length at the time of implantation by removing material from the rod first end 14.

A connector 22, 42 is attached to the first end 14, 24 of each rod 12, 32 and is configured to fix the first end 14, 24 to a boney structure such as a vertebrae 2, ribs 3, or the pelvic bone 4. For example, the connector 22, 42 may be attached to the first end using a fastener 50 that passes through a throughhole (not shown) that extends through the rod 12 in a direction transverse to the longitudinal axis 24. The connector 22, 42 is a fastener that is selected based on the type, location and condition of the boney structure to be fastened. For example, the connector 22, 42 may be one of, but is not limited to, a bone screw, a hook, a cradle, or custom bracket.

In the spinal implant 10, the first rod 12 is arranged to extend in parallel to, and spaced apart from, the second rod 32. In addition, at least a portion of the second end 36 of the second rod 32 overlaps the second end 16 of the first rod 12 when viewed along an axis transverse to the longitudinal axis 24. The second ends 16, 36 of each rod 12, 32 extend through respective throughchannels 62, 64 provided in the housing 61, which houses and supports the spring-loaded mechanism 100 that urges the rods 12, 32 in opposed directions parallel to the longitudinal axis 24, and prevents retraction of the rods 12, 32 relative to the housing.

Figure 3:
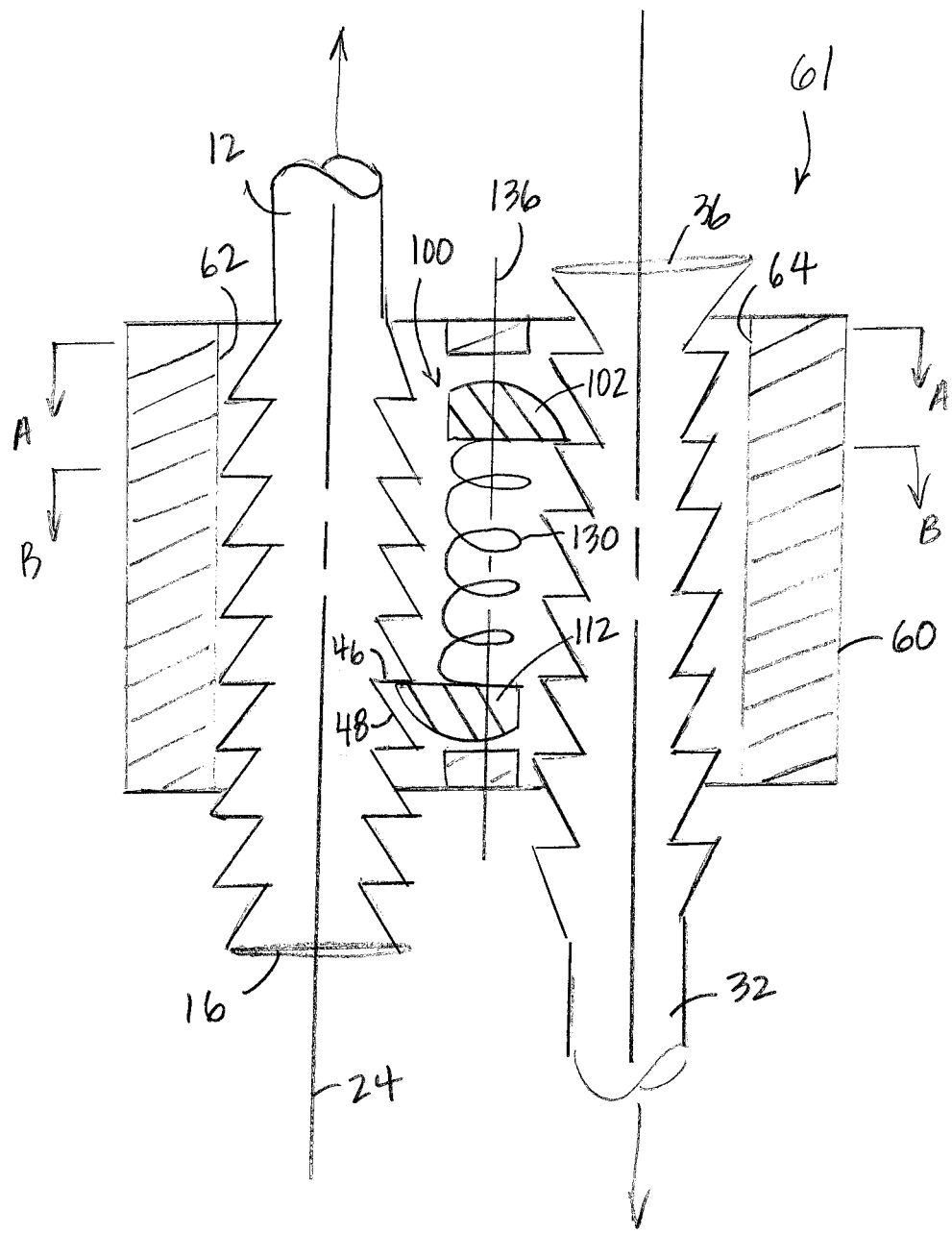
FIG. 3 is a cross-sectional view of the housing of the spinal implant of FIG. 1.

Referring to FIGS. 2 and 3, the coupling 60 includes a housing 61 and the spring-loaded mechanism disposed in the housing 61. The housing 61 is generally rectangular and includes the two throughchannels 62, 64. The throughchannels 62, 64 are parallel to each other, and are also spaced apart in a direction corresponding to a width of the housing 61 (e.g., in a direction transverse to the longitudinal axis 24 of the first rod 12). Each of the throughchannels 62, 64 has a diameter that is dimensioned to receive one of the rods 12, 32 so as to permit free movement of the rod 12, 32 along its respective longitudinal axis 24, 44, but to prevent substantial transverse movement. The housing 61 has a length dimension, corresponding to the length of the throughchannels 62, 64, that is sufficient to maintain the desired parallel relationship between the first rod 12 and the second rod 32, and to accommodate the spring loaded mechanism 100.

The coupling 60 includes an internal passageway 70 disposed generally centrally within the housing 61 that provides a connection between the respective throughchannels 62, 64. The spring-loaded mechanism 100 is disposed in the passageway 70, and is thus able to simultaneously engage the respective toothed portions of both of the rods 12, 32. Aside from the openings corresponding to the throughchannels 62, 64, the housing 61 is closed on all sides, whereby the spring-loaded mechanism 100 is retained within the housing.

Figure 4:
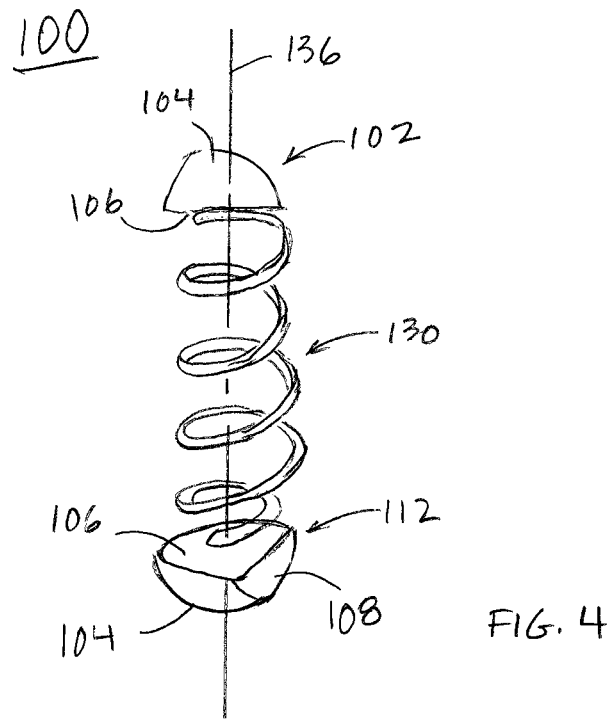
FIG. 4 is an isolated perspective view of the spring-loaded mechanism of the housing of FIG. 1.
Figure 5:
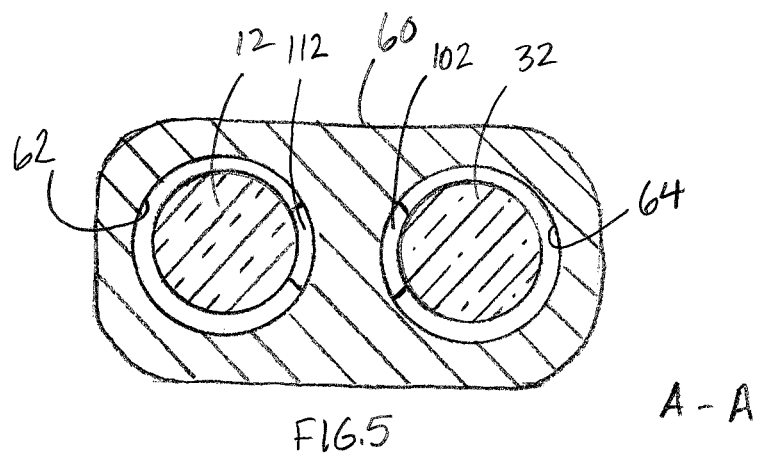
FIG. 5 is a cross-sectional view of the housing of the spinal implant of FIG. 1 as seen along line A-A of FIG. 3.
Figure 6:
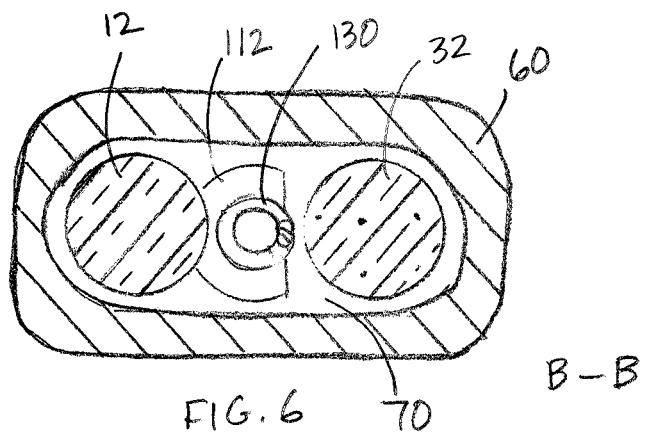
FIG. 6 is a cross-sectional view of the housing of the spinal implant of FIG. 1 as seen along line B-B of FIG. 3.

Referring to FIGS. 4-6, the spring-loaded mechanism 100 includes a first latch 102 and a second latch 112 that are connected by a coil spring 130. The spring-loaded mechanism 100 is disposed in the passageway 70 in such a way that the spring longitudinal axis 136 is parallel to the throughchannels 62, 64 and thus also the longitudinal axis 24 of the first rod 12. The coil spring 130 includes a first end that is connected to the first latch 102, and a second end that is opposed to the first end and connected to the second latch 112.

The first latch 102 and the second latch 112 are each generally semi-spherical, including a base surface 106, and a convex surface 104 opposed to the base surface. A portion of the arcuate periphery of each latch 102, 112 is truncated, forming a side surface 108 that is perpendicular to the base surface 106. The side surface 108 has a linear edge in common with the base surface 106, and a curved edge in common with the convex surface 104.

The coil spring 130 is non-rotatably connected to the base surface 106 of each latch 102, 112. The latches 102, 112 are arranged relative to the coil spring 130 so that the convex surface 104 faces outward in a direction corresponding to the spring longitudinal axis 136. In addition, the latches 102, 112 are further arranged so that the respective side surfaces 108 face outward in a direction corresponding to an axis transverse to the spring longitudinal axis 136. In particular, the respective side surfaces 108 of the first latch 102 and the second latch 112 face in opposed directions.

In the illustrated embodiment, when the spring-loaded mechanism 100 is disposed in the passageway 70, the coil spring 130 is under tension such that the first latch 102 is urged toward the second latch 112 by the spring force. In addition, the base surface 106 of the first latch 102 engages a tooth 40 of the second rod 32, and the base surface 106 of the second latch 112 engages a tooth 40 of the first rod 12. The portion of the base surface 106 that contacts the tooth 40 corresponds to the curved periphery at a location that is furthest from the side face 108. As a result, the spring force of the coil spring 130 is transferred to the teeth 40 via the respective latches 102, 112, and the rods 12, 32 are urged in opposed directions that are parallel to the first rod longitudinal axis 24.

In this configuration, the flat surface 108 of the first latch 102 faces the first rod 12 but is spaced apart from the outer surface of the first rod 12. Similarly, the flat surface 108 of the second latch 112 faces the second rod 32 but is spaced apart from the outer surface of the second rod 32. Thus, by providing the latches 102, 112 with the truncated peripheral shape, it is possible for the first latch 102 to engage the teeth 40 of the second rod 32 without interfering with the axial movement of the first rod 12 within the throughchannel 62. Likewise, it is possible for the second latch 112 to engage with the teeth 40 of the first rod 12 without interfering with the axial movement of the second rod 32 within the throughchannel 64.

In addition, the latches 102, 112 are configured to permit the implant 10 to accommodate growth that results in increased separation of the first rod first end 14 relative to the second rod first end 34. Specifically, when a latch 102, 112 is engaged with a rod tooth 40, the curved convex surface 104 of the latch 102 faces the rod tooth inclined surface 48. The convex surface 104 serves as a sliding surface, whereby the convex surface 104 of the latch 102, 112 and the inclined surface 48 of the tooth 40 are permitted to slide past each other in the direction of growth. At the same time, the engagement of the tooth flat transverse surface 46 with the correspondingly flat base surface 106 prevents retraction of the rods 12, 32 in the direction opposed to the direction of growth.

Figure 8:
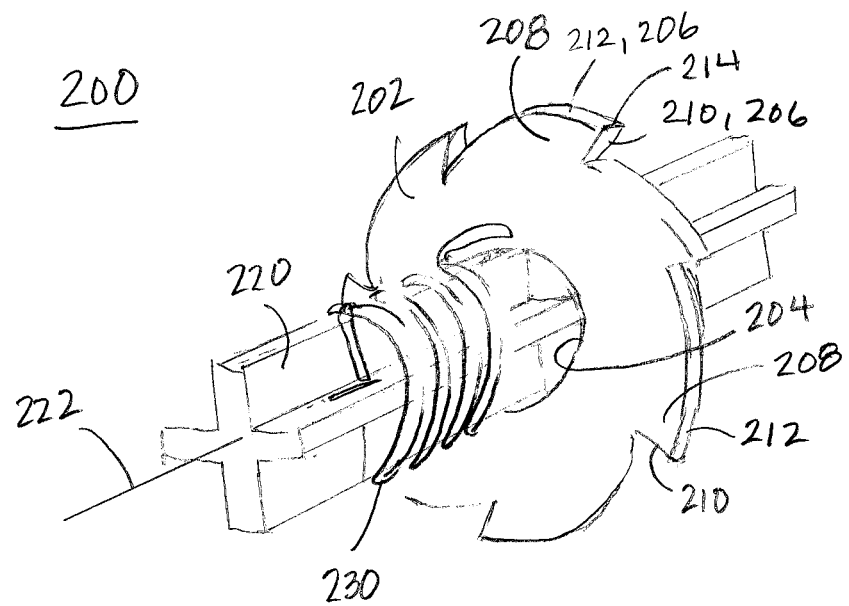
FIG. 8 is an isolated perspective view of the spring-loaded mechanism of the housing of FIG. 7.
Figure 9:
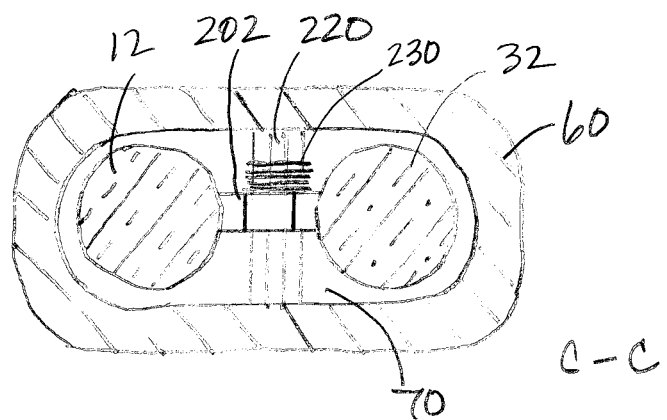
FIG. 9 is a cross-sectional view of the housing of the spinal implant as seen along line C-C of FIG. 7.
Figure 7:
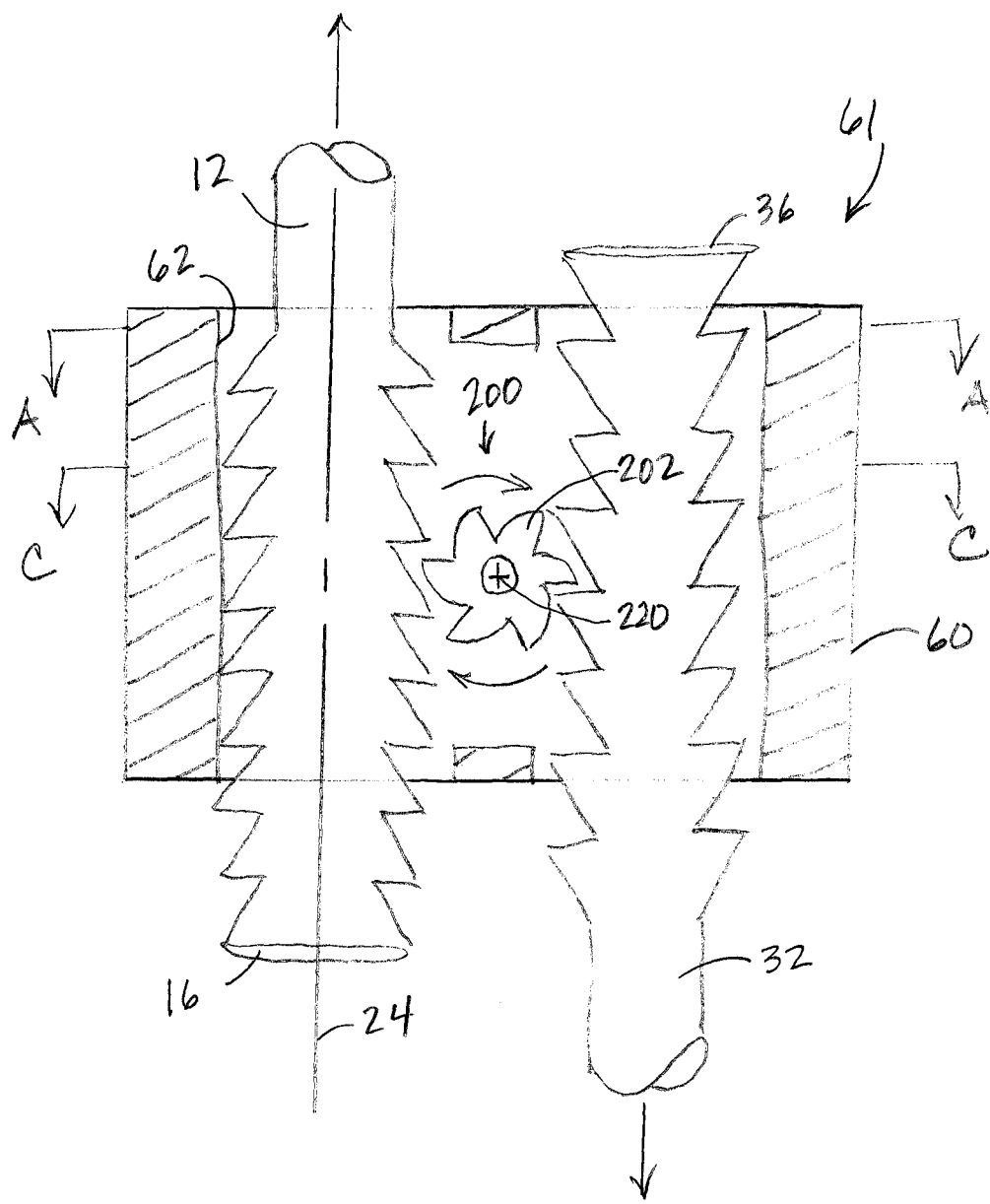
FIG. 7 is a cross-sectional view of another embodiment of the housing of the spinal implant.

Referring to FIGS. 7-9, an alternative embodiment spring-loaded mechanism 200 is disposed in the passageway 70 of the housing 61. The spring loaded mechanism 200 includes a ratchet 202, a spindle 220 that rotatably supports the ratchet 202 within the housing 61, and a torsion spring 230 that connects the ratchet 202 to the spindle 220 and urges the ratchet 202 to rotate relative to the spindle 220 about a spindle longitudinal axis 222.

Referring to FIG. 8, the ratchet 202 is a thin plate having a central opening 204 and a generally circular peripheral edge 206. The peripheral edge 206 includes ratchet teeth 208 that extend about a circumference of the ratchet 202. In the illustrated embodiment, each tooth 208 has a flat side 210, and a curved side 212 that intersects with the flat side at a tooth apex 214. The flat side 210 extends generally radially, and the curved side 212 extends generally circumferentially. The central opening 204 receives the spindle 220, and is dimensioned to receive the spindle 220 with minimum clearance to permit free rotation of the ratchet 202 about the spindle axis 222.

The spindle 220 extends between and is fixed to opposed interior surfaces of the passageway 70. The torsion spring 230 is connected at one end to the ratchet 202, and at an opposed end to the spindle 220, and is wound to drive the ratchet 202 about the spindle axis 220 in a direction toward the ratchet teeth flat side 210 (e.g., in a clockwise direction for the orientation shown in FIG. 6).

Referring again to FIG. 7, in the illustrated embodiment, when the spring-loaded mechanism 200 is disposed in the passageway 70, the ratchet 202 is disposed centrally within the passageway 70 and is dimensioned so that the ratchet teeth 208 engage the rod teeth 40 of both the first rod 12 and second rod 32 simultaneously. In addition, the torsion spring 230 is under tension such that the ratchet tooth flat side 210 is urged against the respective rod tooth transverse surface 46 by the spring force. As a result, the spring force of the torsion spring 230 is transferred to the teeth 40 via the ratchet 202, and the rods 12, 32 are urged in opposed directions that are parallel to the first rod longitudinal axis 24.

In addition, the ratchet 202 is configured to permit the implant 10 to accommodate growth that results in increased separation of the first rod first end 14 relative to the second rod first end 34. Specifically, when a ratchet tooth 208 is engaged with a rod tooth 40, the curved side 212 of the ratchet tooth 208 generally faces the inclined surface 48 of the adjacent rod tooth 40. The curved side 212 of the ratchet tooth 208 serves as a sliding surface whereby the ratchet teeth 208 and the inclined tooth surfaces 48 are permitted to slide past each other in the direction of growth. At the same time, the engagement of the tooth flat transverse surface 46 with the correspondingly flat base surface 106 prevents retraction of the rods 12, 32 in the direction opposed to the direction of growth.

Although the illustrated embodiment shows a single spinal implant used to treat scoliosis, more than one spinal implant can be used. For example, a spinal implant can be implanted on each of the concavely curved side A and the convexly-curved side B of the spine to provide a distracting force on both sides of the spine.

Although the spinal implant 10 has been described herein as being configured to provide distraction between boney structures within the body, the invention is not limited to this configuration. In particular, in some embodiments, the spinal implant 10 can be configured to provide compression between boney structures within the body rather than distraction. Moreover, both types of spinal implant could be used at the same time. For example, a distracting spinal implant can be implanted on the closely-spaced ribs 3a corresponding to the concavely-curved side A of the spinal column, while a compressing spinal implant is implanted on the widely-spaced ribs 3b corresponding to the convexly-curved side B of the spinal column.

A selected illustrative embodiment of the invention is described above in some detail. It should be understood that only structures considered necessary for clarifying the present invention have been described herein. Other conventional structures, and those of ancillary and auxiliary components of the system, are assumed to be known and understood by those skilled in the art. Moreover, while a working example of the present invention has been described above, the present invention is not limited to the working example described above, but various design alterations may be carried out without departing from the present invention as set forth in the claims.

What is claimed is:

1. A spinal implant configured to provide distraction between a first bone and a second bone, the spinal implant comprising:
    a first rod having a first end configured to be connected to the first bone, a second end opposed to the first end, and a first rod longitudinal axis that passes through the first and second ends;
    a second rod having a first end configured to be connected to the second bone, a second end opposed to the first end, and a second rod longitudinal axis that is non-coaxial with the first rod longitudinal axis, at least a portion of the second end of the second rod overlapping the second end of the first rod when viewed along an axis transverse to the first rod longitudinal axis, and
    a coupling that connects the second end of the first rod to the second end of the second rod, the coupling configured to urge the first rod and the second rod in opposed directions that are parallel to the first rod longitudinal axis, the coupling including a mechanism disposed in a passage and configured to engage both the first rod and the second rod, the mechanism having:
    a first latch member,
    a second latch member, and
    an elastic member disposed between the first latch member and the second latch member, the elastic member configured to urge the first latch member and the second latch member in opposed directions that are parallel to the first rod longitudinal axis.

2. The spinal implant of claim 1 wherein the coupling comprises:
    a housing including
        a first throughchannel extending through the housing, and a portion of the first rod is disposed in the first throughchannel;
        a second throughchannel extending through the housing in parallel with, and spaced apart from, the first throughchannel, and a portion of the second rod is disposed in the second throughchannel; and
        the passage extending between and connecting the first throughchannel to the second throughchannel.

3. The spinal implant of claim 1, wherein the second end of the first rod and the second end of the second rod each include teeth configured to cooperatively engage with a corresponding one of the first latch member and the second latch member.

4. The spinal implant of claim 1, wherein each latch member comprises a planar side that connects to the elastic member, and an outwardly-protruding convex side opposed to the planar side.

5. The spinal implant of claim 4, wherein the convex side is truncated to form a flat surface that is perpendicular to the planar side.

6. The spinal implant of claim 1, wherein the elastic member is a coil spring including a spring first end that is connected to the first latch member, and a spring second end that is connected to the second latch member.

7. A spinal implant configured to provide distraction between a first bone and a second bone, the spinal implant comprising:
    a housing;
    a first throughchannel extending through the housing;
    a second throughchannel extending through the housing in parallel with and spaced apart from the first throughchannel,
    a passage within the housing that extends between and connects the first throughchannel to the second throughchannel,
    a first rod disposed in the first throughchannel, the first rod having a first end configured to be connected to the first bone, a second end opposed to the first end, and a first rod longitudinal axis that passes through the first and second ends;
    a second rod disposed in the second throughchannel, the second rod having a first end configured to be connected to the second bone, a second end opposed to the first end, at least a portion of the second end of the second rod overlapping the second end of the first rod when viewed along an axis transverse to the first rod longitudinal axis, and a mechanism disposed in the passage, the mechanism connecting the second end of the first rod to the second end of the second rod, the mechanism configured to urge the first rod and the second rod in opposed directions that are parallel to the first rod longitudinal axis, the mechanism including:

a first latch member, a second latch member, and an elastic member disposed between the first latch member and the second latch member, the elastic member configured to urge the first latch member and the second latch member in opposed directions that are parallel to the first rod longitudinal axis.

8. The spinal implant of claim 7, wherein the second end of the first rod and the second end of the second rod each include teeth configured to cooperatively engage with a corresponding one of the first latch member and the second latch member.

9. The spinal implant of claim 7, wherein each latch member comprises a planar side that connects to the elastic member, and an outwardly-protruding convex side opposed to the planar side.

10. The spinal implant of claim 9, wherein the convex side is truncated to form a flat surface that is perpendicular to the planar side.

11. The spinal implant of claim 7, wherein the elastic member is a coil spring including a spring first end that is connected to the first latch member, and a spring second end that is connected to the second latch member.

\* \* \* \* \*